United States Patent
Andjelic et al.

(10) Patent No.: US 9,296,145 B2
(45) Date of Patent: Mar. 29, 2016

(54) ABSORBABLE POLY (P-DIOXANONE-CO-GLYCOLIDE) MONOFILAMENT FIBERS POSSESSING MID-TERM STRENGTH RETENTION POST-IMPLANTATION

(71) Applicant: Ethicon, Inc., Somerville, NJ (US)

(72) Inventors: Sasa Andjelic, Nanuet, NY (US); Kenneth Keilman, Hillsborough, NJ (US); Dennis D. Jamiolkowski, Long Valley, NJ (US)

(73) Assignee: Ethicon, Inc., Somerville, NJ (US)

( * ) Notice: Subject to any disclaimer, the term of this patent is extended or adjusted under 35 U.S.C. 154(b) by 90 days.

(21) Appl. No.: 14/068,226

(22) Filed: Oct. 31, 2013

(65) Prior Publication Data

US 2015/0119935 A1 Apr. 30, 2015

(51) Int. Cl.
| | |
|---|---|
| *A61B 17/04* | (2006.01) |
| *B29C 47/00* | (2006.01) |
| *D01D 5/098* | (2006.01) |
| *A61B 17/06* | (2006.01) |
| *A61L 17/12* | (2006.01) |
| *B29C 47/86* | (2006.01) |
| *B29C 47/88* | (2006.01) |
| *B29K 73/00* | (2006.01) |
| *B29L 31/00* | (2006.01) |

(52) U.S. Cl.
CPC .............. *B29C 47/0014* (2013.01); *A61B 17/04* (2013.01); *A61B 17/06166* (2013.01); *A61L 17/12* (2013.01); *B29C 47/0004* (2013.01); *B29C 47/0061* (2013.01); *B29C 47/0064* (2013.01); *B29C 47/0066* (2013.01); *B29C 47/0088* (2013.01); *B29C 47/862* (2013.01); *B29C 47/8805* (2013.01); *D01D 5/098* (2013.01); *B29K 2073/00* (2013.01); *B29K 2995/006* (2013.01); *B29K 2995/0056* (2013.01); *B29L 2031/726* (2013.01); *B29L 2031/731* (2013.01); *B29L 2031/753* (2013.01)

(58) Field of Classification Search
CPC .. A61B 17/06166; A61B 17/04; A61L 17/00; A61L 17/12; C08G 63/664; C08G 63/08; C08G 63/64
USPC .............. 606/230; 156/244.11; 264/103, 164, 264/320
See application file for complete search history.

(56) References Cited

U.S. PATENT DOCUMENTS

| | | | |
|---|---|---|---|
| 4,653,497 A | 3/1987 | Bezwada et al. | |
| 6,794,484 B2 | 9/2004 | Newman et al. | |
| 6,831,149 B2 | 12/2004 | Newman et al. | |
| 8,262,963 B2 | 9/2012 | Kennedy et al. | |
| 8,353,931 B2 * | 1/2013 | Stopek et al. | 606/228 |
| 2007/0035061 A1 | 2/2007 | Ghen et al. | |

* cited by examiner

*Primary Examiner* — Jonathan W Miles
*Assistant Examiner* — George L Ulsh
(74) *Attorney, Agent, or Firm* — E. Richard Skula (57) ABSTRACT

Novel absorbable monofilament sutures and fibers having unique and improved properties are disclosed including mid-term strength retention post-implantation. Also disclosed is a novel method of manufacturing absorbable monofilament sutures and fibers. The sutures and fibers are extruded from poly(p-dioxanone-co-glycolide) copolymers.

53 Claims, 3 Drawing Sheets

A graph of *in vitro* Breaking Strength Retention (BSR) data in pounds as a function of time (37°C/ pH=7.4) of inventive and comparative 92/8 PDO/Gly monofilaments.

Fig. 1

Figure 2. Schematic presentation of monofilament extrusion line described in the Prior art: U.S. 4,653,497

Figure 3. A graph of *in vitro* Breaking Strength Retention (BSR) data in pounds as a function of time (37°C/ pH=7.4) of inventive and comparative 92/8 PDO/Gly monofilaments.

ABSORBABLE POLY (P-DIOXANONE-CO-GLYCOLIDE) MONOFILAMENT FIBERS POSSESSING MID-TERM STRENGTH RETENTION POST-IMPLANTATION

TECHNICAL FIELD

The field of art to which this invention relates is absorbable sutures, more specifically absorbable monofilament surgical sutures made from absorbable polymers having novel properties, including in vivo properties.

BACKGROUND OF THE INVENTION

Surgical sutures and attached surgical needles are well known in the art for use in a variety of conventional surgical procedures. For example, such sutures may be used to approximate tissue about incisions or lacerations in epidermal layers and underlying fascia layers, join blood vessel ends, attach tissue to medical devices such as heart valves, repair body organs, repair connective tissue, etc. Conventional surgical sutures may be made from known biocompatible materials, particularly synthetic and natural biocompatible polymeric materials, which may be non-absorbable or absorbable. Examples of synthetic non-absorbable polymeric materials useful to manufacture non-absorbable sutures include polyesters, polyolefins, polyvinylidene fluorides and polyamides. Examples of synthetic absorbable polymeric materials useful to manufacture absorbable sutures include polymers and copolymers made from lactones such as the lactides, glycolide, p-dioxanone, ϵ-caprolactone, and trimethylene carbonate. The term absorbable is meant to be a generic term, which may also include bioabsorbable, resorbable, bioresorbable, degradable or biodegradable.

Absorbable sutures are preferred by surgeons for use in many surgical procedures because of several advantages and properties possessed by such sutures. Absorbable sutures must be capable of providing the desired tensile strength in vivo for a sufficient period of time to allow for effective tissue healing. Wound healing is dependent on the nature of the specific tissue as well as the healing characteristics of the individual undergoing the surgical procedure. For example, poorly vascularized tissue is likely to heal more slowly than highly vascularized tissue; likewise, diabetic patients and the elderly tend to heal more slowly as well. There are thus opportunities to provide suture materials that can match the healing characteristics of a variety of wounds. Any implant, such as a suture, appears as a foreign body to the patient's immune system. Upon absorption of an absorbable suture the polymeric material comprising the suture is eliminated from the body, thus providing, it is believed, a better patient outcome. The outcome may be improved for several reasons including decreased post-operative pain, reduced risk of long-term infections, and better patient comfort. In addition, it is known that implantable medical devices, including sutures, may provide a platform for the attachment of bacteria and the subsequent formation of bacterial biofilms. The absorption and elimination of absorbable sutures may result in a significant diminishment of infections and decreased biofilm formation at the wound site.

Absorbable sutures may be manufactured as monofilament sutures or as braided multifilament sutures. Monofilament sutures are of particular interest because of several advantageous properties, including less infection potentiation, better knot sliding, less tissue drag and, in general, less tissue reactions attributable to overall smaller surface area. Multifilament sutures have associated advantages as well including flexibility or hand, and knot security characteristics. Multifilament sutures may have disadvantages in certain aspects of their use. One particular perceived disadvantage of a braided multifilament suture is the tendency to wick fluids along the length of the suture. This is believed by some to be attributable to the presence of interstices between the braided filaments that create a fluid pathway. This fluid pathway may allow bacteria to readily travel with fluids along the length of the suture as fluids are wicked along this fluid pathway with the possibility of an infection moving along the length of implanted suture at the tissue repair site. Another disadvantage is that multifilament sutures must be braided from smaller diameter fibers, adding another manufacturing step.

It is to be understood that if an absorbable polymer can be made into a successful multifilament suture, it may not necessarily be made into a successful monofilament suture. Monofilament sutures must be based upon polymers that exhibit an inherent softness; this characteristic is often reflected in a low glass transition temperature ($T_g$). Thus a very successful multifilament suture based on 10/90 poly((L-)-lactide-co-glycolide) would not generally make a successful monofilament suture because this copolymer has a glass transition temperature above room temperature, rendering monofilament fibers of any substantial diameter quite stiff.

Another important aspect of an absorbable polymer, if it is to be made into a monofilament suture, is the need for it to be dimensionally stable. Thus, as the molecular orientation of the polymer is increased during fiber processing to increase strength, the driving force to shrink and deform is increased. This is particularly problematic with low glass transition temperature polymers used to make monofilament sutures. Dimensional stability is provided to the suture by virtue of the rapid crystallization of the polymer during fiber formation. Accordingly, the highly oriented polymer of a strong monofilament suture is prevented from shrinking or deforming due to the presence of this morphological characteristic—sufficient crystallinity.

Absorbable sutures are designed to have the requisite physical characteristics to assure desirable and efficacious in vivo behavior. Specifically, the sutures need appropriate tensile strength during the required healing period; this is typically characterized as breaking strength retention. As the advantages of absorbable sutures continue to become more recognized and accepted, there is a need for sutures having different breaking strength retention profiles that are matched to the differing tissue requirements presented in a variety of surgical procedures. In order to obtain the required design properties, it is necessary to provide absorbable polymers and manufacturing processes that will yield absorbable sutures with the required properties.

The retention of mechanical properties post-implantation is often a very important and critical feature of an absorbable medical device. The device must retain mechanical integrity until the tissue has healed sufficiently. In some bodily tissues, healing occurs more slowly, requiring an extended retention of mechanical integrity. As mentioned earlier, this is often associated with tissue that has poor vascularization. Likewise there are other situations in which a given patient may be prone to poor healing, e.g., the diabetic patient. There are, however, many situations in which rapid healing occurs, which require the use of fast absorbing medical devices such as sutures; this is often associated with excellent vascularization. Examples of instances where such fast absorbing sutures can be used include, but are not limited to, certain pediatric surgeries, oral surgery, repair of the peritoneum after an episiotomy, and superficial wound closures.

When rapid healing occurs, the mechanical retention profile of the medical device could reflect a more rapid loss in properties. Concomitant with this is the rate of absorption (bioabsorption or resorption), that is, the time required for the medical device to disappear from the surgical site.

Absorbable polymers for use in absorbable sutures and manufacturing processes for such sutures have been disclosed in the art in order to provide improved absorbable sutures.

Bezwada, et al. in U.S. Pat. No. 4,653,497 describes crystalline p-dioxanone and glycolide copolymers and surgical devices therefrom.

The problem of slow crystallization rates in glycolide-containing copolymers was addressed in U.S. Pat. No. 6,794,484 and U.S. Pat. No. 6,831,149. These patents disclose the use of specific ratios of mono- to difunctional initiators to generate copolymers that have significantly faster nucleation rates compared to copolymers made from either monofunctional or difunctional initiators alone. Among other glycolide containing copolymer compositions, a 92/8 poly(p-dioxanone-co-glycolide) (PDO/Gly) copolymer prepared from dodecanol and diethylene glycol in a molar ratio of 50:50 was described. Medical devices including sutures made from such copolymers were disclosed.

U.S. Pat. No. 8,262,963 discloses a process for making absorbable filaments from copolymers of glycolide and an alkylene carbonate such as trimethylene carbonate.

U.S. Pub. No. U.S. 2007/0035061 discloses a method of making absorbable microtubes from bioabsorbable polymers and copolymers.

Although existing absorbable sutures are adequate for their use in certain surgical procedures, there is a need in this art for novel surgical sutures having improved properties, in particular absorbable monofilament sutures that provide high tensile strength with lower Young's modulus, breaking strength retention (BSR) suitable for mid-term surgical applications, excellent knot sliding and knot security behavior, while still possessing good pliability/handling properties.

The need in this art for novel absorbable monofilament sutures exhibiting a breaking strength retention (BSR) suitable for mid-term surgical applications will now be addressed. There exist monofilament sutures, exemplified by MONOCRYL™ suture which is commercially available from Ethicon, Inc. (Somerville, N.J.), which lose their strength in a rather short time frame, approximately three weeks. There are many surgical repairs that heal within this timeframe and this is a very useful product class. For tissue that requires a very long time to heal, however, extended wound healing support must be provided. For very long fixation needs, a monofilament based on poly(p-dioxanone) homopolymer is commercially available, PDS II™ suture (Ethicon, Inc., Somerville, N.J.). This product loses all of its tensile strength between about 14 and 16 weeks post-implantation for suture sizes 4/0 to 2/0. What does not presently exist is a monofilament suture possessing a mid-term BSR profile in which all strength is lost between about 4 weeks and about 10 weeks, post-implantation. Novel sutures having these properties are desired to address these needs.

Also, there is a need for novel processes for making such novel monofilaments sutures. Such sutures would be useful in both existing surgical procedures where absorbable sutures are used, and would also be indicated for other surgical procedures and in patients where conventional absorbable sutures are less desirable. These surgical situations include slow-to-heal tissues, immune compromised patients, diabetic patients, and geriatric patients.

SUMMARY OF THE INVENTION

Accordingly, novel absorbable monofilament sutures are disclosed. The sutures have a straight tensile strength of at least 80 Kpsi, a Young's Modulus of less than 200 Kpsi, and a breaking strength retention profile (BSR) of at least 50% at three weeks post-implantation and at least 30% at four weeks post-implantation. The sutures are made from a poly(p-dioxanone-co-glycolide) copolymer. The mole percent of polymerized p-dioxanone in the copolymer is from about 90 mole percent to about 94 mole percent, and the mole percent of polymerized glycolide in the copolymer is from about 6 mole percent to about 10 mole percent. The copolymer is made utilizing a mixture of a monofunctional polymerization initiator and a difunctional polymerization initiator at a mole ratio of monofunctional to difunctional initiator of from about 40/60 to about 60/40.

Another aspect of the present invention is a novel method of manufacturing novel absorbable monofilament sutures having improved properties.

Still yet another aspect of the present invention is a novel absorbable monofilament suture manufactured by the novel method of the present invention.

These and other aspects and advantages of the present invention will become more apparent from the following description and accompanying drawings.

DETAILED DESCRIPTION OF THE INVENTION

The absorbable polymers useful in the practice of the present invention include fast crystallizing, low glass transition temperature (below 20° C.) copolymers of p-dioxanone and glycolide in the molar ratio of about 90/10 to about 94/6. It is particularly preferred to use copolymers made using multiple initiators as disclosed in U.S. Pat. Nos. 6,794,484 and 6,831,149, which are incorporated by reference. The absorbable copolymers useful in the practice of the present invention will have an inherent viscosity (IV) ranging typically from about 1.2 dL/g to about 2.4 dL/g, and preferably about 1.4 dL/g to about 2.2 dL/g, most preferably 1.8 dL/g to about 2.0 dL/g. It is to be understood that terms "monofilament suture" and "monofilament fiber" are used interchangeably herein. The absorbable monofilament fibers of the present invention will have an inherent viscosity (IV) typically slightly lower than the copolymer of which they are made, ranging typically from about 1.0 dL/g to about 2.2 dL/g, preferably about 1.3 dL/g to about 2.1 dL/g, most preferably 1.7 dL/g to about 2.0 dL/g. The copolymers useful in the novel sutures of the present invention will typically contain about 90 mole % to about 94 mole % of polymerized p-dioxanone, preferably about 92 mole %. The copolymers useful in the novel sutures of the present invention will typically contain about 6 mole % to about 10 mole % of polymerized glycolide, preferably about 8 mole %. It is particularly preferred to use a 92/8 poly(p-dioxanone/glycolide) (PDO/Gly) block copolymer.

The PDO/Gly copolymers useful in the sutures of the present invention will provide monofilament sutures having a straight tensile strength of at least about 80 Kpsi, a Young's Modulus of less than about 200 Kpsi, a breaking strength retention of at least about 50% at 3 weeks post-implantation and at least about 30% at 4 weeks post-implantation.

The copolymers useful to manufacture the novel absorbable sutures of the present invention may be manufactured in the following manner. Block copolymers of p-dioxanone and glycolide can be prepared by ring-opening polymerization in a conventional reactor vessel outfitted with a suitable agitator, using a catalyst (e.g., stannous octoate) at a monomer-to-catalyst mole ratio of about 30,000:1, utilizing 50:50 mole ratios of mono-functional initiator, for example, dodecanol (DD), to a difunctional initiator, for example, diethylene glycol (DEG). The monomer-to-total initiator ratio value determines the final molecular weight of the copolymer and for the purpose of the present invention 92/8 PDO/Gly copolymers were made with the monomer-to-total initiator ratio of about 800:1 to about 900:1. It is to be understood that variation in the level of the catalyst and in the monomer-to-total initiator ratio can be made without deviating from the spirit and scope of this invention.

A polymerization process that can be used in preparation of the PDO/Gly copolymers useful in the novel monofilament absorbable sutures of the present invention is a two-step polymerization comprising a first stage homopolymerization using 100% p-dioxanone and a second stage block copolymerization with an added monomer composition of 100 mole % glycolide. The first homopolymerization step is typically conducted at temperatures from about 100° C. to about 120° C. lasting for about 4-6 hours. The second copolymerization step is typically conducted at about 130° C.-150° C. for additional 1-2 hours. After the second stage, unreacted p-dioxanone and glycolide monomers (typically between 10% and 20%) can be removed by a vacuum drying procedure. The overall final composition of dried samples, as determined by $^1$H NMR analysis, provide a copolymer of about 92 mole % polymerized p-dioxanone and about 8 mole % polymerized glycolide. In order to achieve this desired chemical composition, the initial monomer charge will be slightly higher in p-dioxanone monomer: about 94 mole % PDO and about 6 mole % glycolide.

Alternatively, the discharged resin produced and described above, may be placed in a nitrogen purged oven and heated in a solid state fashion for about 48 hours to about 80 hours at temperatures of approximately 80° C. This step may be conducted in attempt to further increase the monomer conversion or/and increase the molecular weight of the resin. After the solid state polymerization treatment, the resin can be processed using identical procedures described for reactor-only produced resin.

Figure 1:
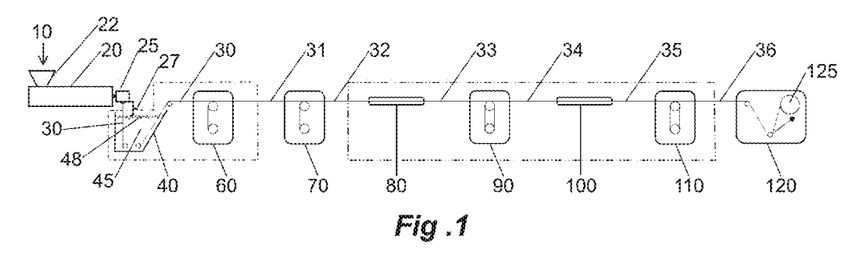
FIG. 1 is a flow diagram of a novel process of the present invention used to produce the novel monofilament sutures of the present invention.

The novel fiber forming process of the present invention is diagrammatically illustrated in the flow diagram of FIG. 1. An absorbable polymer composition 10 useful to manufacture the novel sutures of the present invention is fed into the nitrogen purged hopper 22 of extruder 20. The polymer 10 is then heated, melted and worked by the extruder 20 such that it is in a flowable state. The molten polymer 10 is then discharged from the outlet 25 of the extruder 20 in the form of a monofilament fiber extrudate 30.

The fiber extrudate 30 is pulled into the quench bath 40 containing chilled water 45; although a wide range of quench bath temperatures can be employed, a temperature of 20° C. is particularly preferred. The "air gap" 27, which is the distance between the bottom of extruder outlet 25 and the water surface 48 of the quench bath 40, will typically range from about 0.25 inches to about 4.0 inches. An air gap of about 1" to about 3" is particularly preferred. The fiber extrudate 30 resides in the water media 45 of the quench bath 40 for a sufficient period of time to effectively provide the required polymer morphology, particularly crystal nucleation, of the polymer chains of fiber extrudate 30. The residence time of the extrudate fiber 30 in the water media 45 of the quench bath 40 is controlled by the line speed of the extrudate fiber 30 and the path length of the extrudate fiber 30 within the water media 45. The residence time of the extrudate fiber 30 in the water media 45 of the quench bath 40 is typically from about 1 second to a few minutes (e.g., about 3 minutes), more typically about 30 seconds to a few minutes. The level of crystallinity of the fiber 30 after exiting the quench bath 40 needs to be low enough, i.e., sufficiently low, to allow a maximum draw ratio during the subsequent drawing steps of at least 7.5. If the level of crystallinity of the fiber 30 exiting the bath 40 is too high, the fiber breaks if one tries to achieve the higher draw ratio, limiting the molecular orientation and thus the tensile strength of the fiber. The fiber extrudate 30 then moves to the rolls of godet 60 and then to the rolls of godet 70; the relative linear speed of the rolls of godet 70 to godet 60 is greater than or equal to about 5.5. The fiber, 31, undergoing drawing between godet 60 and godet 70 is thus drawn to a ratio of greater than or equal to about 5.5. The godets 60 and 70 may be optionally heated (e.g., from about 30° C. to 90° C.) to allow for smoother drawing. Optionally, the filament is subjected to additional process steps in order aid fiber drawing, to increase the percentage of crystallinity and to provide dimensional stability. As shown in FIG. 1, the filament 32 is next moved to an optional first hot air oven 80 where it is heated to a sufficiently effective temperature (from about 100° C. to 130° C.) for a sufficiently effective residence time in order to provide sufficient crystal growth in fiber 33. The residence time in the hot air oven 80 is controlled by the line speed of the fiber 32/33 and the path length of the fiber within the hot air oven 80. The fiber 32 playing off the rolls of godet 70, in addition to optionally undergoing heat treatment in hot air oven 80, may also undergo further drawing by employing godet 90. The draw ratio between godet 90 and godet 60 will typically be about 7.5 or greater. Optionally, the rolls of godet 90 can be heated (from about 30° C. to 90° C.) to allow for easier drawing. The filament 34 emerging from the rolls of optional godet 90 is then moved to a second hot air oven 100, again heated to a sufficiently effective temperature (from about 100 to 130° C.) for a sufficiently effective residence time in order to achieve optimal polymer morphology resulting in drawn fiber 35. The fiber 34 playing off the rolls of godet 90, in addition to optionally undergoing heat treatment in hot air oven 100, may also undergo further drawing or relaxation by employing godet 110, again resulting in drawn fiber 35. The draw ratio between godet 90 and godet 110 will typically be about 0.8 to about 1.2. The resulting filament 36 is then moved to take up unit 120 where the filament is collected on roll 125. The filament 36 collected on roll 125 can be stored in a nitrogen or vacuum chamber until further use.

In order to mature polymer morphology to enhance dimensional stability even further and to possibly reduce the level of residual monomer the filaments or portions of the filament on roll 125 may optionally be placed on an annealing rack and put in a heated oven equipped with a nitrogen purge for an additional annealing step at a sufficiently effective annealing temperature. The annealing temperature for the fibers of the current invention may be in the range from about 60° C. to about 95° C. for a sufficiently effective time, e.g., about six hours of residence time. Preferably, a certain amount of fiber relaxation is desired (5%-10%) to lower the fiber's Young's modulus, to further improve pliability and handling of the resulting suture. Alternately the initial tension of the racked fiber may be adjusted to help prevent the loss of molecular orientation (0% relaxation).

We have discovered that the length of time between the fiber orientation step and the fiber annealing step may be important in achieving a low Young's modulus in the final product. It has been observed that conducting the annealing step no later than about 48 hours after the orientation step results in a softer fiber (lower Young's modulus) that a fiber annealed well after this time frame. By way of example, a size 2/0 monofilament fiber of the present invention exhibited a Young's modulus of 150,000 psi prior to annealing. If the oriented fiber is rack annealed [at 85° C. for 6 hours using 5% relaxation] after an extended storage time (9 months at room temperature under vacuum), the modulus of the annealed fiber increased to about 250,000 psi. When the oriented fiber is rack annealed under the same annealing conditions, but no later than about 48 hours after the orientation step, the Young's modulus observed for the annealed fiber was less than 150,000 psi, and the fiber was felt to be softer, an advantageous outcome.

Figure 2:
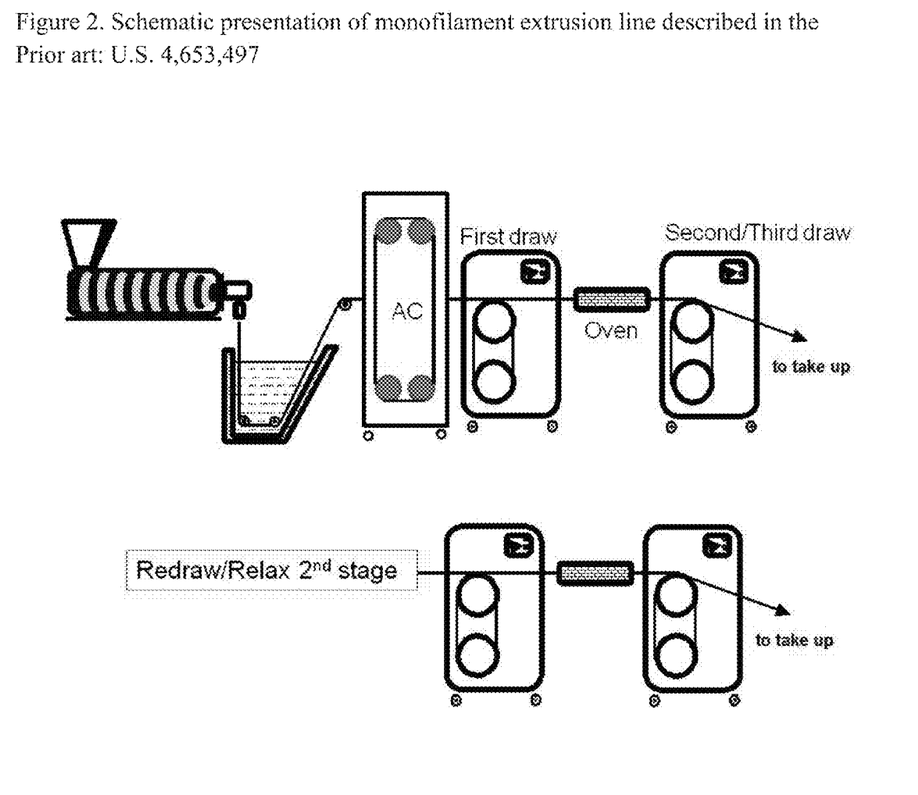
FIG. 2 illustrates a process of the prior art. The extrusion is described by a two-stage process with additional element(s) prior to the drawing step (first stage) to enhance the crystallization level of an extrudate before drawing.

As a comparison to the novel process of the present invention, the process flow described in prior art U.S. Pat. No. 4,653,497 is diagrammatically illustrated in FIG. 2. It contains an additional heated air cabinet located just after the water bath, which serves to generate more crystallinity in an extrudate before a first drawing step. If the fiber crystallinity before drawing is too low, this results in a fiber that cannot withstand much loading to effectively draw and further crystallize, or sag on the fiber line, or outright break. Also, it can shrink significantly in the later stages of a process losing its molecular orientation and consequently its tensile strength. The process of the prior art described in FIG. 2 contains the second, redrawing and relaxation step to achieve desired final properties of a drawn fiber. Before the second, redraw/relax step, the fiber from step 1 was placed in a vacuum chamber for 16 hours. In contrast, the process flow of copolymers of the current invention eliminates this second, drawing/relaxing step.

The process equipment that can be used in the processes of the present invention will be conventional equipment that is readily commercially available. An example of an extruder that is useful in the practice of the present invention is a Davis-Standard extruder, model no. 22450, available from Davis-Standard, Cedar Grove, N.J., USA. An example of godets useful in the practice of the present invention is a J J Jenkins godet, model no. 9397, available from J J Jenkins, Inc., Matthews, N.C., USA. An example of a hot air oven useful in the practice of the present invention is a J J Jenkins oven, model no. 74DM1115-3 available from J J Jenkins, Inc., Matthews, N.C., USA. An example of a take-up unit useful in the practice of the present invention is a Georg Sahm take-up unit, model no. 283 E, manufactured by Georg Sahm GmbH, Eschwege, Germany.

The monofilament sutures of the present invention may contain if desired medically useful substances. The medically useful substances may be incorporated into or onto the sutures in a variety of conventional manners including compounding, coating, spraying, dipping, sputtering and the like. The monofilament sutures of the present invention may be delivered to the surgeon in a variety of lengths. Preferably, conventional surgical needles are mounted to one end or both ends of the sutures (i.e., single-armed or double-armed), although the sutures may be unarmed with no surgical needles mounted.

The medically useful substances that may be incorporated in the surgical sutures of the present invention include antimicrobials, therapeutic agents, antibiotics, and other components or agents.

If desired, the monofilament sutures or fibers of the present invention may contain other conventional medically useful components and agents. The other components, additives or agents will be present to provide additional desired characteristics to the monofilament sutures of the present invention including but not limited to antimicrobial characteristics, controlled drug elution, therapeutic aspects, radio-opacification, and enhanced osseointegration.

The surgical sutures may also include other conventional additives including dyes, radio-opaque agents, growth factors and the like. The dye should be generally acceptable for clinical use with absorbable polymers; this includes, without limitation, D&C Violet No. 2 and D&C Blue No. 6 and similar combinations thereof. Additional dyes that are useful include conventional dyes useful with absorbable polymers including D&C Green No. 6, and D&C Blue No. 6.

The variety of therapeutic agents that can be used in the polymer blends of the present invention is vast. In general, therapeutic agents which may be administered via compositions of the invention include, without limitation, anti-infectives, such as antibiotics and antiviral agents.

Such other components will be present in a sufficient amount to effectively provide for the desired effects or characteristics. Typically, the amount of the other adjuncts will be about 0.1 weight percent to about 20 weight percent, more typically about 1 weight percent to about 10 weight percent and preferably about 2 weight percent to about 5 weight percent.

Examples of antimicrobial agents useful with the sutures of the present invention include the polychlorophenoxy phenols such as 5-chloro-2-(2,4-dichlorophenoxy)phenol (also known as Triclosan). Examples of radio-opacification agents include barium sulfate while examples of osseointegration agents include tricalcium phosphate.

The variety of therapeutic agents that can be used with the sutures of the present invention is vast. In general, therapeutic agents which may be administered via pharmaceutical compositions of the invention include, without limitation, antiinfectives, such as antibiotics and antiviral agents; analgesics and analgesic combinations; anorexics; antihelmintics; antiarthritics; antiasthmatic agents; adhesion preventatives; anticonvulsants; antidepressants; antidiuretic agents; antidiarrheals; antihistamines; anti-inflammatory agents; antimigraine preparations; contraceptives; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators, including general coronary, peripheral and cerebral; central nervous system stimulants; cough and cold preparations, including decongestants; hormones, such as estradiol and other steroids, including corticosteroids; hypnotics; immunosuppressives; muscle relaxants; parasympatholytics; psychostimulants; sedatives; tranquilizers; naturally derived or genetically engineered proteins, polysaccharides, glycoproteins, or lipoproteins; oligonucleotides, antibodies, antigens, cholinergics, chemotherapeutics, hemostatics, clot dissolving agents, radioactive agents and cystostatics. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the realm of one skilled in the art to determine an advantageous profile, depending on the therapeutic conditions to be treated.

Suitable glasses or ceramics that may be incorporated into the sutures of the present invention include, but are not limited to phosphates such as hydroxyapatite, substituted apatites, tetracalcium phosphate, alpha- and beta-tricalcium phosphate, octacalcium phosphate, brushite, monetite, metaphosphates, pyrophosphates, phosphate glasses, carbonates, sulfates and oxides of calcium and magnesium, and combinations thereof.

Modern surgical sutures generally range from Size 5 (heavy braided suture for orthopedics) to Size 11/0 (for example, a fine monofilament suture for ophthalmics). The actual diameter of thread for a given U.S.P. size differs depending on the suture material class. The diameters of sutures in the synthetic absorbable suture class are listed in the United States Pharmacopeia (USP) as well as in the European Pharmacopoeia. The USP standard is more commonly used. The novel sutures of the present invention can be made in a variety of sizes, including conventional suture sizes. The suture sizes of the monofilament sutures of the present invention will range from 10-0 to 5. The monofilament fibers of the present invention when used for constructing other medical devices such as meshes, etc., will typically have diameters in the range of about 1 to about 8 mils. Multifilament sutures when constructed from the fibers of the present invention will have a sufficiently effective denier per filament (dpf) to provide the desired properties, typically a dpf of about 0.5 to about 5.

The novel monofilament sutures of the present invention may be packaged in conventional suture packaging including polymer tray with tracks, paper folders, etc., with a polymer and/or foil overwrap that is hermetically sealed and impervious to moisture and microbes. The sutures will be sterilized preferably in their packages using conventional medical device sterilizations processes, such as ethylene oxide, radiation, autoclaving, etc. Those skilled in the art will understand that the optimal sterilization process chosen will not adversely affect the characteristics of the absorbable polymeric sutures.

The novel absorbable sutures of the present invention that are made from the novel absorbable polymer filaments are preferably useful as monofilament surgical sutures. However, the filaments may be used in other conventional medical devices including, but not limited to, fibrous devices such as multifilament-based sutures and surgical fabrics including meshes, woven fabrics, nonwoven fabrics, knitted fabrics, fibrous bundles, cords, tissue engineering substrates, and the like. The surgical meshes may be made using conventional methods including knitting, weaving, air-laying, etc.

In one embodiment, the present invention consists of an absorbable multifilament suture, made of a poly(p-dioxanone-co-glycolide) copolymer of the present invention, wherein the mole percent of polymerized p-dioxanone is from about 90 to about 94, the mole percent of polymerized glycolide is from about 6 mole percent to about 10 mole percent, the copolymer made utilizing a monofunctional polymerization initiator and a difunctional polymerization initiator at a mole ratio of monofunctional initiator to difunctional initiator of from 40/60 to 60/40, wherein said suture has a straight tensile strength of at least 80 Kpsi. For example, the absorbable multifilament suture has a dpf (denier per filament) from about 0.5 to about 5.

If desired, the monofilament sutures of the present suture may be processed to have barbs. Such barbs can be emplaced or incorporated in a conventional manner including cutting, molding, pre-forming, forming, attaching, etc. An example of a barb-forming process is disclosed in the U.S. Pat. No. 8,216, 497 "Tissue Holding Devices and Methods for Making the Same" which is incorporated herein by reference. An alternate process of making barbed sutures is a cutting process. An example of a barb-cutting process is disclosed in the U.S. Pat. No. 7,913,365 "Method of Forming Barbs on a Suture and Apparatus for Performing Same" which is incorporated herein by reference.

The following examples are illustrative of the principles and practice of the present invention although not limited thereto.

Example 1

Synthesis of Block 92/8 PDO/Gly Copolymer Used in the Present Invention

A series of PDO/Gly block copolymers were prepared by ring-opening polymerization in a clean, dry, stainless steel, oil-heated, jacketed reactor equipped with a mechanical agitator using stannous octoate (total Tin 29% w/w) at a monomer-to-catalyst mole ratio of 30,000:1, utilizing 50:50 mole ratios of mono-functional initiator, dodecanol (DD), to a difunctional initiator, diethylene glycol (DEG). The monomer-to-total initiator ratio value determines the final molecular weight of the copolymer. Two 92/8 PDO/Gly copolymers will be described: a) Example 1A, with a monomer-to-total initiator ratio of 825:1, and, b) Example 1B, with a monomer-to-total initiator ratio of 900:1.

The polymerization process used in preparation of the PDO/Gly copolymers was a two-step polymerization comprising a first stage homopolymerization using 100% p-dioxanone and a second stage block copolymerization with an added monomer composition of 100 mole % glycolide. In the first stage of a typical PDO/Gly polymerization, a specified amount of p-dioxanone, stannous octoate catalyst solution (in toluene), DD and DEG (50/50 DD/DEG mole ratio), and a dye (D&C Violet #2, 0.04 wt. %) were charged under a nitrogen purge to a clean, dry stainless steel, oil-heated, jacketed reactor equipped with a mechanical agitator. After charging a reactor, the first step was to lower the pressure to less than one Torr for about 20 minutes, after which nitrogen gas was introduced to raise the pressure slightly over atmospheric. The evacuation/nitrogen purge process was repeated using a 25-minute vacuum-hold period. The constituents were heated under constant agitation to 110° C. and then maintained at this temperature for about four and one-half hours.

In the second stage, the temperature of the oil entering the outer jacket of the reactor was then increased to 135° C. The glycolide monomer was previously melted in the melt tank at 115° C. and transferred to the reactor containing polymerized PDO under nitrogen purge. The stirrer speed was increased to 20 RPM for the first 15 minutes of the second-stage to enhance blending of ingredients. The polymerization was continued typically for about one hour and fifteen minutes. The resulting block copolymer was discharged into aluminum or Teflon coated trays. When copolymer discharge was complete, the trays were placed in nitrogen curing oven set at room temperature to cool down overnight. The next day the resin was placed into storage bags, weighed and transferred to freezer storage. The frozen polymer was subsequently ground using ³⁄₁₆" screen and then sieved using #18 screen sieve. The copolymer was then dried under vacuum at elevated temperature. Generally, residual glycolide monomer in all dried copolymers usually ranges from about 0.1 to about 0.2 mole percent as revealed by $^1$H NMR, while residual p-dioxanone monomer concentration usually ranges from about 0.20 to about 0.80 mole percent again as revealed by $^1$H NMR.

The drying procedure was carried out in a Patterson-Kelley tumble dryer. After charging the resin, the dryer was closed, and the pressure was reduced to less than 200 mTorr. Once the pressure was below 200 mTorr, the dryer rotation was activated at a rotational speed of 10 RPM with no heat for 10 hours. After the 10 hour period, the oil jacket temperature was set to 65° C. with drying at this temperature for 4 hours. The oil temperature was again raised, this time to 75° C.; this period lasted 4 hours. The final heating period was employed at 85° C. for 24 hours. At the end of the final heating period, the batch was allowed to cool for a period of 2 hours while maintaining rotation and vacuum. The polymer was discharged from the dryer by pressurizing the vessel with nitrogen, opening the discharge valve, and allowing the polymer granules to descend into waiting vessels for long term storage. The overall final composition of dried samples, as determined by $^1$H NMR analysis, provided a copolymer of about 92 mole % polymerized p-dioxanone and about 8 mole % polymerized glycolide. In order to achieve this desired chemical composition, the initial monomer charge was slightly higher in p-dioxanone monomer: 94 mole % PDO and 6 mole % glycolide. Due to the high sensitivity of these copolymers to hydrolytic degradation, materials were stored under vacuum and tested under strict dry nitrogen conditions.

The final selected properties of dried 92/8 PDO/Gly copolymer resins that were made according to this Example (and used in Examples 3A and 3B) are shown in Table 1.

Example 3

Monofilament Extrusion of Block 92/8 PDO/Gly Copolymers

Monofilament extrusion runs of the PDO/Gly block copolymers of Examples 1A and 1B useful in the practice of the present invention were conducted using a one inch Davis-Standard Extruder with a 24:1 barrel length equipped with a single grooved feed throat. The block copolymers were processed in accordance with the method described previously herein and illustrated in FIG. 1. A water bath tank capable of heating up to about 50° C., three sets of orientation godets (with heating capability) with one additional relaxation godet at the end of line prior to a collection spool were utilized. Between the second and third godet, and also between the third godet and the final relaxation godet, were two annealing ovens used to heat the fibers to enhance its polymer morphology. Depending on the particular run (inventive vs. comparative), an air cabinet capable of heating up to 60° C. was optionally used. This piece of equipment was placed between the water bath and the first godet with a goal to develop enough crystallinity in a material before an initial drawing

TABLE 1

Selected Properties of Dried 92/8 PDO/Gly Copolymers of the Present Invention

| Copolymer ID | IV* (dL/g) | Mw** (g/mol) | MI*** (g/10 min) | Polymerized PDO (mole %) | Polymerized Gly (mole %) | PDO Monomer (mole %) | Glycolide Monomer (mole %) |
|---|---|---|---|---|---|---|---|
| Example 1A | 1.63 | 60k | 0.212 | 91.7 | 7.5 | 0.7 | 0.2 |
| Example 1B | 1.95 | 74k | 0.099 | 91.6 | 7.7 | 0.6 | 0.1 |

*Inherent Viscosity was determined in hexafluoroisopropanol (HFIP) solution at 25° C. at concentration of 0.1 g/dL.
**Weight Average Molecular Weight as determined by GPC
***Melt Index measurements (MT987 Extrusion Plastometer, Tinius Olsen, Willow Grove, PA, USA) were conducted at 150° C. using 6,600 g weight disc. The die diameter was 0.0260 inches, while the die length was 0.315 inches.

Example 2

Synthesis of Block 92/8 PDO/Gly Copolymer with a Single Initiator—Comparative Example The polymerization scheme of this comparative example was identical to that of Example 1 except the initiator used was DEG only. Monomer to initiator ratio was 900:1. The final dried PDO/Gly copolymer resin had the following properties shown in Table 2:

step. If the amount of crystallinity in a resin is too low at this point, the fiber will break or exhibit very low strength at the end of extrusion. The fiber diameter was measured inline using a Mitutoyo Lasermac (laser micrometer) located just before a collection spool.

In this example, for each copolymer run, the bath temperature was set at 20° C., the speed ratios of the godets is listed below. The monofilaments sutures had a suture size of 2/0, corresponding to the fiber diameter about 14.2 mils.

TABLE 2

Selected Properties of Dried 92/8 PDO/Gly Copolymers Made with a Single Initiator

| Copolymer ID | IV* (dL/g) | $M_w$ (g/mol) | MI** (g/10 min) | Polymerized PDO (mole %) | Polymerized Gly (mole %) | PDO Monomer (mole %) | Glycolide Monomer (mole %) |
|---|---|---|---|---|---|---|---|
| Example 2 | 1.75 | 65k | 0.149 | 91.4 | 7.5 | 0.9 | 0.1 |

*Inherent Viscosity was determined in HFIP solution at 25° C. at concentration of 0.1 g/dL.
**Weight Average Molecular Weight as determined by GPC
***Melt Index measurements (MT987 Extrusion Plastometer, Tinius Olsen, Willow Grove, PA, USA) were conducted at 150° C. using 6,600 g weight disc. The die diameter was 0.0260 inches, while the die length was 0.315 inches.

The extruded monofilaments of the present invention were next collected on spools and stored in a vacuum chamber. In order to ensure dimensional stability, selected 92/8 PDO/Gly monofilaments were rack annealed at 85° C. for six hours using 5% relaxation to obtain a final fiber length is 95% of its initial length.

Selected extrusion conditions with tensile physical properties of various drawn and annealed monofilaments are listed in Tables 3A-B.

morphology for fibers to be drawn at higher molecular orientation (see for instance the properties for Example 3B-2B-Comparative in Tables 3A-B). It is important to stress that the reference US 2007/0035061 A1 that describes the formation of absorbable microtubes teaches away from using an air gap higher than 0.5" because of high standard deviations of the outer diameter. However, for the monofilament processes of the present invention involving 92/8 PDO/Gly resin having an

TABLE 3A

Selected Extrusion Conditions for 92/8 PDO/Gly Size 2-0 Monofilaments[1, 2]

| Sample ID | Polymer Resin Description | Air Gap (inch) | Die Temp (° C.) | Air cabinet Temp (° F.)/ # of passes | Temp of Hot Air Oven One & Two (° C.) | $2^{nd}$ Godet Roller Temp (° C.) |
|---|---|---|---|---|---|---|
| Example 3A-1-Inventive | Example 1A, IV = 1.63 dL/g | ¼" | 130 | Not used | 110 & 110 | No heat |
| Example 3B-1-Comparative | Example 1B IV = 1.95 dL/g | ¼" | 125 | 150/1 | 115 & 110 | 60 |
| Example 3B-2-Comparative | Example 1B IV = 1.95 dL/g | ¼" | 125 | RT/1 | 110 & 110 | No heat |
| Example 3B-2B-Comparative | Example 1B IV = 1.95 dL/g | ¼" | 115 | Not used | 100 & 110 | 65 |
| Example 3B-3-Inventive | Example 1B IV = 1.95 dL/g | 2.0" | 130 | Not used | 115 & 120 | 60 |
| Example 3B-4-Inventive | Example 1B IV = 1.95 dL/g | 3.5" | 125 | Not used | 115 & 120 | 60 |
| Example 3C-5-Comparative-1 | Example 2 IV = 1.73 dL/g | 0.5" | 120 | 85/1 | 90 & 90 | No heat |
| Example 3C-5-Comparative-2 | Example 2 IV = 1.73 dL/g | 1.0" | 150 | 85/1 | 90 & 90 | No heat |

[1]the die size for each run was 70/1
[2]the water bath for each run was set at 20° C.

TABLE 3B

Extrusion Conditions, Physical Properties and related Observations of Drawn 2-0 Monofilaments of Example 3

| Sample ID | Max Draw/ Total Draw Ratios | Straight Tensile (lbs)/ Elong. (%) | Observations |
|---|---|---|---|
| Example 3A-1-Inventive | 7.50/6.45 | 14.5/43% | Good fiber d = 14.34 mil, Knot Strength, KS = 7.0; Speed Godet #2 = 130 fpm; Young's Modulus, YM = 160 kpsi |
| Example 3B-1-Comparative | 5.50/4.68 | 10.3/36% | Line breaks constantly, strength lower with higher cabinet T; KS = 5.2 lbs.; YM = 95 kpsi |
| Example 3B-2-Comparative | 5.75/4.89 | 8.10/32% | Removed heat from the cabinet, Speed Godet #2 = 95, but line breaks at $2^{nd}$ Godet; YM = 100 kpsi |
| Example 3B-2B-Comparative | 6.00/4.80 | 10.1/48% | No air cabinet, Speed Godet #2 = 95, but line again breaks at $2^{nd}$ - still too much crystallinity |
| Example 3B-3-Inventive | 7.50/6.30 | 15.2/40% | Good fiber, d = 14.13 mil, KS = 7.0; Speed Godet #2 = 115 fpm; YM = 150 kpsi |
| Example 3B-4-Inventive | 8.00/6.72 | 17.3/40% | Good strong fiber, d = 14.13 mil, KS = 7.6; Speed Godet #2 = 120 fpm; YM = 165 kpsi |
| Example 3C-5-Comparative-1 | 6.50/5.55 | 6.06/24% | Very weak fiber, d = 14.20 mil Speed Godet #2 = 90 fpm; YM = 156 kpsi |
| Example 3C-5-Comparative-2 | NA | NA | Very elastic, sticky fibers, unable to thread through air cabinet due to back wraps |

It was surprisingly and unexpectedly observed that for higher IV resins useful in the practice of the present invention (IV=1.95 dL/g) significantly higher air gap values (up to 3.5") are needed to draw the fiber to high molecular orientation, and consequently higher tensile strength. As shown in Tables 3A-B, for the 92/8 PDO/Gly resin having an IV of 1.95 dL/g an air gap less than 2" could not produce suitable polymer IV of 1.95 dL/g the preferable air gap range was found to be between 2 and 4". An air gap larger than 4" was found to be not suitable because of the higher instability of a fiber diameter obtained during processing.

In addition, the data indicated that drawing fibers to a very high extent in the first stages of the drawing (5.5× and more) resulted in fibers having high tensile strength.

Finally, it is shown in Tables 3A-B that a 92/8 PDO/Gly copolymer made by a single initiator only (Example 2) failed to produce the high fiber properties of the fibers of the present invention despite utilizing a wide range of processing conditions, including the use of an air cabinet. The copolymer resin of Example 2 nucleated and crystallized too slow during the processing, preventing the fiber to "lock in" the needed polymer morphology to keep its molecular orientation at a higher level.

The copolymer resins of the current invention made from the mixed initiator approach (combination of mono- and difunctional initiators) can be examined for the presence of specific initiators in the following way. First, an absorbable copolymer can be placed in a buffer solution and the copolymer allowed to fully hydrolyze. To speed up the process, higher temperatures or higher pH values of a solution media can be used. Next, the final products of hydrolysis can be examined using standard and conventional analytical methods, including NMR, IR, mass spectroscopy, etc. Using these methods the type and concentration of initiators used in the synthesis can be easily and readily determined.

Example 4

Physical Properties of Drawn and Annealed 92/8 PDO/Gly 2-0 Monofilaments

Selected fibers whose physical properties and extrusion conditions are described in Tables 3A-B were annealed under specified conditions and their tensile properties examined using an Instron tensile testing apparatus. The Instron tester (Instron Corporation Model 5944, Norwood, Mass. USA) operated at a crosshead speed of 12 inches/minute having a gauge length of 5 inches with a weight of 450 lbs. The properties are shown in Table 4.

TABLE 4

Tensile Properties of Selected Drawn and Annealed 2-0 PDO/Gly Monofilaments

| Sample ID | Description | Dia. (mils) | Tensile Strength (lbs) | Tensile Strength (Kpsi) | Elongation (%) | Knot (lbs) | Young's Modulus (Kpsi) |
|---|---|---|---|---|---|---|---|
| Example 3A-1-Annealed | Annealed at 85° C. for 6 h with 5% rack relaxation | 14.5 | 14.4 | 87.2 | 50.9 | 6.8 | 145 |
| Example 3B-3-Annealed | Annealed at 85° C. for 6 h with 5% rack relaxation | 14.2 | 15.2 | 96.0 | 46.6 | 6.9 | 164 |
| Example 3B-4-Annealed | Annealed at 85° C. for 6 h with 5% rack relaxation | 14.2 | 16.5 | 104 | 41.1 | 7.6 | 180 |

Note:
Young's modulus of 90/10-97/3 PDO/Gly fibers in Bezwada ref. were in the range of 150-300 Kpsi.

Example 5

Thermal Stability of the Resin of the Present Invention

Differential Scanning calorimetry (DSC) data on 92/8 PDO/Gly Resin (Example 1A), drawn fiber made from Example 1A before annealing (Example 3A-1-Inventive) and after an annealing step (Example 3A-1-Annealed) is shown in Table 5. The Differential Scanning calorimeter used was a TA Instruments (New Castle, Del. USA) Model Q20 equipped with fifty-position robotic autosampler.

TABLE 5

Characterization of Selected Resin, Unannealed, and Annealed Fiber

| Polymer ID | NMR Total Residual Monomer (mole %) | First heat* | | | Second heat** | | | |
|---|---|---|---|---|---|---|---|---|
| | | $T_{g1}$ (° C.) | $T_{m1}$ (° C.) | $\Delta H_m$ (J/g) | $T_{g2}$ (° C.) | $T_{m2}$ (° C.) | $T_C$ (° C.) | $\Delta H_C$ (J/g) |
| Example 1A, lower IV dried resin | 0.9 | −1.5 | 102.0 | 79.6 | −6.0 | 102.0 | 61.0 | 42.0 |
| Example 2A-1-Inventive, Unannealed fiber from Example 1A | 1.0 | 3.8 | 101.0 | 72.0 | −6.8 | 100.5 | 57.4 | 46.7 |
| Example 2A-1-Annealed, Annealed fiber from Example 1A | 0.7 | 6.5 | 101.2 | 72.5 | −6.3 | 100.4 | 58.5 | 44.5 |

*the first heat DSC measurements were conducted at a heating rate of 10° C./min
**the material is first melted at 140° C., than quenched (at a rate of −60° C./min) to −60° C., followed by heating at a rate of 10° C./min It is evident from Table 5 that a 92/8 PDO/Gly copolymer used in the novel absorbable monofilament sutures of the current invention undergoes no significant morphological changes (degradation, transesterification, etc.) during various steps of thermal processing. This includes the ability of material to crystallize fast, which is shown by the second heat DSC data in Table 5. Fast crystallization is important to provide a robust and reliable manufacturing process to enable the very high strength exhibited by the inventive fibers, as well as allowing for high retention of mechanical strength as a function of time post-implantation.

Example 6

Breaking Strength Retention (BSR) Data of Drawn and Annealed 92/8 PDO/Gly 2-0 Monofilaments In vitro BSR measurements for Example 3A-1-Annealed, Example 3B-3-Annealed, and Example 3B-4-Annealed were conducted at physiologically relevant in vitro conditions: 7.27 pH buffer solution maintained at 37° C. temperature. The data was used for BSR evaluations in pounds and percentages. At specified time points, the tensile strength of samples was tested using Instron material testing machine. The test parameters were 1 inch gauge length and 1 inch per minute crosshead speed. Also obtained was in vivo BSR data on Example 3A-1-Annealed monofilament. The data indicated excellent agreement between in vitro and in vivo data for this copolymer system. BSR for the rest of the samples was obtained using the in vitro method only. Tensile strength measurements made to determine breaking strength retention were performed using the Instron's tester apparatus having a crosshead speed of 1.0 in/min and a gauge length of 1 inch. The summary of BSR data on various inventive 2-0 92/8 PDO/Gly monofilaments are presented in Table 6. As a comparison, corresponding in vivo BSR data described in the prior art (U.S. Pat. No. 4,653,497) with the wide range of PDO/Gly copolymer compositions covered (90/10-97/3 PDO/Gly) is shown in Table 6 as well. Comparative data in Table 6 was obtained using the same Instron testing parameters as those described in the current invention.

TABLE 6

In Vitro BSR Data Expressed in Percentages and in Corresponding Pounds on Drawn and Annealed 92/8 PDO/Gly 2-0 Monofilaments

| Time (days) | Example 3A-1-Annealed (Based on Lower IV Resin) | Example 3B-3-Annealed (Based on Higher IV Resin) | Example 3B-4-Annealed (Based on Higher IV Resin) | Ref. Bezwada [90/10-97/3 PDO/Gly] |
|---|---|---|---|---|
| 0 | 100% (13.3 lbs) | 100% (14.1 lbs) | 100% (16.2 lbs) | NA |
| 7 | 78% (10.3) | 81% (11.5) | 80% (12.9) | NA |
| 14 | 66% (8.8) | 73% (10.3) | 71% (11.5) | NA |
| 21 | 46% (6.1) | 58% (8.2) | 53% (8.6) | 30-50% (NA) |
| 28 | 21% (2.8) | 34% (4.9) | 31% (5.1) | 10-30% (NA) |
| 35 | 8% (1.1) | 14% (2.0) | 15% (2.5) | NA |
| 42 | 5% (0.6) | 9.1% (1.3) | 6.7% (1.1) | NA |
| 49 | 2% (0.3) | 4.3% (0.6) | 3.5% (0.6) | NA |

Compared to BSR data from the prior art (U.S. Pat. No. 4,653,497), taken at the 3 and 4 week time period, two samples of higher IV copolymers of the present invention (Example 3B-3-Annealed and Example 3B-4-Annealed) resulted in fibers having higher BSR that those described in the prior art. Considering the fact that the compositional range of PDO/Gly fibers in U.S. Pat. No. 4,653,497 bearing those BSR properties listed in Table 6 is rather wide (90/10 to 97/3), this represents a significant improvement for this critical parameter. This point bears clarification. Fibers based on the 97/3 PDO/Gly of '497 are expected to exhibit a much longer BSR profile than the fibers based on the 90/10 PDO/Gly of '497. That is, as the glycolide content increases, the ability to hold strength post-implantation decreases. One may then conclude that the 50% BSR at 21 days mentioned in '497 is associated with the polymer having the lower glycolide content (3%) and that the 30% BSR at 21 days mentioned in '497 is associated with the polymer having the higher glycolide content (10%). The copolymer compositions of the present invention are directed toward polymerized glycolide between about 6% to about 10%, yet still exhibit a BSR typically greater than about 50% at 21 days post-implantation and 30% at 28 days post-implantation. Even when the molecular weight of the resin is relatively lower, the 21 days post-implantation BSR is greater than about 45%.

In addition, all three 92/8 PDO/Gly fibers of the current invention show measureable BSR strength even up to 7 weeks post-implantation, which may be important and clinically relevant for patients having compromised healing properties.

Figure 3:
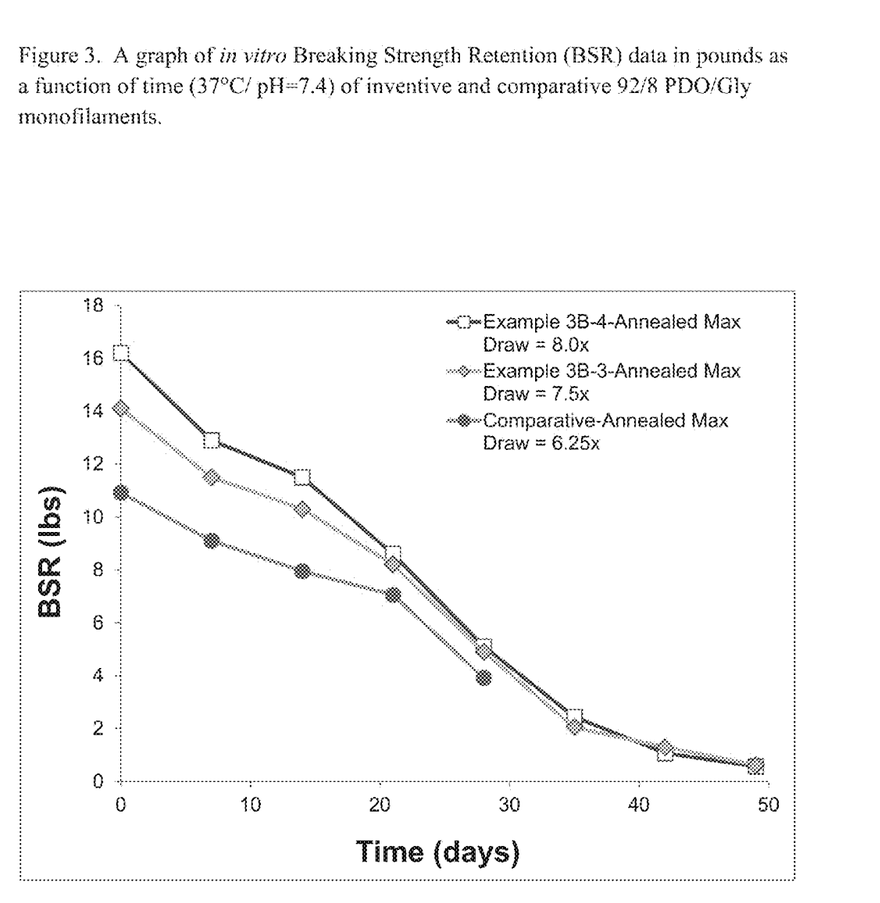
FIG. 3 is a graph of in vitro Breaking Strength Retention (BSR) data in pounds as a function of time (37° C./pH=7.4) of inventive and comparative 92/8 PDO/Gly monofilaments.

Next, as an illustration of improved processing steps of the current invention on the BSR properties (in lbs.) of the selected 2-0 drawn and annealed 92/8 PDO/Gly monofilaments made from mixed initiators but with different molecular orientation are shown in FIG. 3. The sample named "Comparative-Annealed Max Draw 6.25x" was made from 92/8 PDO/Gly resin of IV=1.85 dL/g. During the extrusion process of this comparative material, an air gap of ¾" was used along with an air cabinet leading to only a maximum achievable draw ratio of 6.25×. The fiber was annealed using the same conditions as fibers of the present invention. Data in FIG. 3 strongly suggest higher initial tensile strength values and longer BSR profiles for samples drawn to higher extent.

The novel absorbable sutures and fibers of the present invention along with the novel process of the present invention have many advantages. The suture advantages include high tensile strength with lower Young's modulus; breaking strength retention (BSR) profiles suitable for mid-term surgical applications; excellent knot sliding and knot security behavior; and, good pliability/handling properties, all in the form of a traditional (unbarbed) suture, or a barbed suture. Additional fiber advantages include the capability of being barbed by conventional cutting and forming processes, and the capability of being processed into other conventional medical devices, including but not limited to surgical fabrics such as meshes.

Although this invention has been shown and described with respect to detailed embodiments thereof, it will be understood by those skilled in the art that various changes in form and detail thereof may be made without departing from the spirit and scope of the claimed invention.

We claim:

1. An absorbable monofilament suture, comprising:
a poly(p-dioxanone-co-glycolide) copolymer, wherein the mole percent of polymerized p-dioxanone is from about 90 to about 94, the mole percent of polymerized glycolide is from about 6 mole percent to about 10 mole percent, the copolymer made utilizing a monofunctional polymerization initiator and a difunctional polymerization initiator at a mole ratio of monofunctional initiator to difunctional initiator of from about 40/60 to about 60/40,
wherein said suture has a straight tensile strength of at least 80 Kpsi, a Young's Modulus of less than 200 Kpsi, and a breaking strength retention (BSR) of at least 50% at 3 weeks post-implantation and at least 30% at 4 weeks post-implantation.

2. The monofilament suture of claim 1, wherein the poly (p-dioxanone-co-glycolide) copolymer has an inherent viscosity (IV) of about 1.2 to about 2.4 dL/g, as measured in HFIP at 25° C. at a concentration of 0.1 g/dL.

3. The monofilament suture of claim 2, wherein the poly (p-dioxanone-co-glycolide) copolymer has an inherent viscosity (IV) of about 1.4 to about 2.2 dL/g, as measured in HFIP at 25° C. at a concentration of 0.1 g/dL.

4. The monofilament suture of claim 3, wherein the poly (p-dioxanone-co-glycolide) copolymer has an inherent viscosity (IV) of about 1.8 to about 2.0 dL/g, as measured in HFIP at 25° C. at a concentration of 0.1 g/dL.

5. The monofilament suture of claim 1, wherein the copolymer comprises about 92 mole % of poly(p-dioxanone) and about 8 mole % of glycolide.

6. The monofilament suture of claim 1, wherein the mole ratio of monofunctional initiator to difunctional initiator is about 50/50.

7. The monofilament suture of claim 1, additionally comprising a biocompatible dye.

8. The monofilament suture of claim 1, wherein the monofunctional initiator is selected from the group consisting of dodecanol, 1-hexanol, and 1-heptanol.

9. The monofilament suture of claim 1, wherein the difunctional initiator is selected from the group consisting of diethylene glycol, triethylene glycol, 1,6-hexanediol, 1,4 butanediol, and 1,5 pentanediol.

10. The monofilament suture of claim 1, additionally comprising a medically useful substance.

11. The monofilament suture of claim 10, wherein the medically useful substance comprises an antimicrobial.

12. The monofilament suture of claim 11, wherein the medically useful substance comprises Triclosan.

13. The monofilament suture of claim 1, wherein the suture has a suture size ranging from about Size 5 to about Size 11/0.

14. The monofilament suture of claim 1, additionally comprising a surgical needle mounted to an end.

15. The monofilament suture of claim 1, additionally comprising a coating.

16. The monofilament suture of claim 1, wherein the suture additionally comprises at least one barb.

17. The monofilament suture of claim 16, wherein the barb is formed by a process selected from the group consisting of cutting, pre-forming, forming, attaching and molding.

18. A surgical fabric, said fabric comprising the absorbable monofilament suture of claim 1.

19. The monofilament suture of claim 1, wherein the mole percent of polymerized p-dioxanone is about 92, the mole percent of polymerized glycolide is about 8 mole percent, the copolymer is made utilizing dodecanol and diethylene glycol polymerization initiators at a mole ratio of about 50/50, and wherein the copolymer or the suture has an inherent viscosity of about 1.85 to about 1.95 dL/g, as measured in HFIP at 25° C. at a concentration of 0.1 g/dL, and a crystallinity level of the suture is at least 35%.

20. An absorbable monofilament suture, made by the process comprising:
    a) providing an absorbable biodegradable copolymer, the copolymer comprising a poly(p-dioxanone-co-glycolide) copolymer, wherein the mole percent of polymerized p-dioxanone is from about 90 to about 94, the mole percent of polymerized glycolide is from about 6 to about 10, the copolymer made utilizing a monofunctional polymerization initiator and a difunctional polymerization initiator at a mole ratio of monofunctional initiator to difunctional initiator of from about 40/60 to about 60/40;
    b) melting the copolymer in an extruder having a die and extruding the copolymer as a monofilament fiber at extruder and die temperatures ranging from about 100° C. to about 130° C.;
    c) maintaining an air gap between the die and a water surface of a water bath set to from about ¼" to about 4";
    d) guiding the fiber through the water bath set at temperature between about 5° C. and about 30° C.;
    e) moving the fiber to a first set of godets running at a speed Z;
    f) moving the fiber to a second set of godets running at a speed of at least 5.5×Z;
    g) moving the fiber to a heated oven set at a temperature of about 100° C. to about 120° C.;
    h) moving the partially drawn fiber to a third set of godets running at the speed of at least 7.5×Z;
    i) moving the fully drawn fiber to a second heated oven set at a temperature of about 100° C. to about 120° C.;
    j) moving the fully drawn fiber to a fourth set of godets running at the speed of about 6×Z to about 8×Z;
    k) collecting the fiber;
    l) annealing the fiber; and,
    m) relaxing the fiber to about 5% to about 10%,
    wherein, said suture has a straight tensile strength of at least 80 Kpsi, a Young's Modulus of less than 200 Kpsi, and a breaking strength retention (BSR) of at least 50% at 3 weeks post-implantation and at least 30% at 4 weeks post-implantation.

21. The monofilament suture of claim 20, wherein the fiber is maintained in the water bath for a sufficient time such that the fiber has a crystallinity level sufficiently low to allow a total draw ratio of at least 7.5.

22. The monofilament suture of claim 21, wherein the poly(p-dioxanone-co-glycolide) copolymer has an inherent viscosity (IV) of about 1.2 to about 2.4 dL/g, as measured in HFIP at 25° C. at a concentration of 0.1 g/dL.

23. The monofilament suture of claim 22, wherein the poly(p-dioxanone-co-glycolide) copolymer has an inherent viscosity (IV) of about 1.4 to about 2.2 dL/g, as measured in HFIP at 25° C. at a concentration of 0.1 g/dL.

24. The monofilament suture of claim 23, wherein the poly(p-dioxanone-co-glycolide) copolymer has an inherent viscosity (IV) of about 1.8 to about 2.0 dL/g, as measured in HFIP at 25° C. at a concentration of 0.1 g/dL.

25. The monofilament suture of claim 20, wherein the copolymer comprises about 92 mole % of polymerized p-dioxanone and about 8 mole % of polymerized glycolide.

26. The monofilament suture of claim 20, wherein the mole ratio of monofunctional initiator to difunctional initiator is about 50/50.

27. The monofilament suture of claim 20, additionally comprising a biocompatible dye.

28. The monofilament suture of claim 20, wherein the monofunctional initiator is selected from the group consisting of dodecanol, 1-hexanol, and 1-heptanol.

29. The monofilament suture of claim 20, wherein the difunctional initiator is selected from the group consisting of diethylene glycol, triethylene glycol, 1,6-hexanediol, 1,4 butanediol, and 1,5 pentanediol.

30. The monofilament suture of claim 20, additionally comprising a medically useful substance.

31. The monofilament suture of claim 30, wherein the medically useful substance comprises an antimicrobial.

32. The monofilament suture of claim 31, wherein the medically useful substance comprises Triclosan.

33. The monofilament suture of claim 20, wherein the suture has a suture size ranging from about Size 5 to about Size 11/0.

34. The monofilament suture of claim 20, additionally comprising a surgical needle mounted to an end.

35. The monofilament suture of claim 20, additionally comprising a coating.

36. The monofilament suture of claim 20, wherein the suture additionally comprises at least one barb.

37. The monofilament suture of claim 36, wherein the barb is formed by a process selected from the group consisting of cutting, pre-forming, forming, attaching and molding.

38. A surgical fabric, said fabric comprising the absorbable monofilament suture of claim 20.

39. A method of manufacturing an absorbable monofilament suture, comprising the steps of:
   a) providing an absorbable copolymer, the copolymer comprising a poly(p-dioxanone-co-glycolide) copolymer, wherein the mole percent of polymerized p-dioxanone is from about 90 to about 94, the mole percent of polymerized glycolide is from about 6 to about 10, the copolymer made utilizing a monofunctional polymerization initiator and a difunctional polymerization initiator at a mole ratio of monofunctional initiator to difunctional initiator of from about 40/60 to about 60/40;
   b) melting the copolymer in an extruder having a die and extruding the copolymer as a monofilament fiber at extruder and die temperatures ranging from about 100° C. to about 130° C.;
   c) maintaining an air gap between the die and a water surface of a water bath set to from about ¼" to about 4";
   d) guiding the fiber through the water bath set at temperature between about 5° C. and about 30° C.;
   e) moving the fiber to a first set of godets running at a speed Z;
   f) moving the fiber to a second set of godets running at a speed of at least 5.5×Z;
   h) moving the fiber to a heated oven set at a temperature of about 100° C. to about 120° C.;
   h) moving the partially drawn fiber to a third set of godets running at the speed of at least 7.5×Z;
   i) moving the fully drawn fiber to a second heated oven set at a temperature of about 100° C. to about 120° C.;
   j) moving the fully drawn fiber to a fourth set of godets running at the speed of about 6×Z to about 8×Z;
   k) collecting the fiber;
   l) annealing the fiber; and,
   m) relaxing the fiber to about 5% to about 10%,
      wherein, said suture has a straight tensile strength of at least 80 Kpsi, a Young's Modulus of less than 200 Kpsi, and a breaking strength retention (BSR) of at least 50% at 3 weeks post-implantation and at least 30% at 4 weeks post-implantation.

40. The method of claim 39, wherein the fiber is maintained in the water bath for a sufficient time such that the fiber has a crystallinity level sufficiently low to allow a total draw ratio of at least 7.5.

41. The method of claim 39, wherein the second set of Godets is heated to about 40° C. to 80° C.

42. The method of claim 39, wherein the poly(p-dioxanone-co-glycolide) copolymer has an inherent viscosity (IV) of about 1.2 to about 2.4 dL/g, as measured in HFIP at 25° C. at a concentration of 0.1 g/dL.

43. The method of claim 42, wherein the poly(p-dioxanone-co-glycolide) copolymer has an inherent viscosity (IV) of about 1.4 to about 2.2 dL/g, as measured in HFIP at 25° C. at a concentration of 0.1 g/dL.

44. The method of claim 43, wherein the poly(p-dioxanone-co-glycolide) copolymer has an inherent viscosity of about 1.8 to about 2.0 dL/g.

45. The method claim 39, wherein the air gap is from about 1.5 to about 4".

46. The method of claim 39, wherein the fiber is annealed in-line or via a rack process.

47. The method of claim 39, comprising the additional step of forming at least one barb in the suture.

48. The method of claim 47, wherein the barb is formed by a process selected from the group consisting of cutting, preforming, forming, attaching and molding.

49. The method of claim 39 comprising the additional step of making a surgical fabric from the suture.

50. The method of claim 46, wherein the annealed fiber has a crystallinity level of at least 35%.

51. The method of claim 39, wherein the fiber resides in the water bath for a period of time ranging from about 1 second to about 3 minutes.

52. An absorbable multifilament suture, comprising:
   a poly(p-dioxanone-co-glycolide) copolymer, wherein the mole percent of polymerized p-dioxanone is from about 90 to about 94, the mole percent of polymerized glycolide is from about 6 mole percent to about 10 mole percent, the copolymer made utilizing a monofunctional polymerization initiator and a difunctional polymerization initiator at a mole ratio of monofunctional initiator to difunctional initiator of from about 40/60 to about 60/40,
   wherein said suture has a straight tensile strength of at least 80 Kpsi.

53. The absorbable multifilament suture of claim 52, having a dpf from about 0.5 to about 5.

* * * * *